US00PP26941P3

(12) United States Plant Patent
Ciccolella

(10) Patent No.: US PP26,941 P3
(45) Date of Patent: Jul. 12, 2016

(54) ***DIANELLA CAERULEA* PLANT NAMED 'DCGL'**

(50) Latin Name: *Dianella caerulea*
Varietal Denomination: DCGL

(71) Applicant: Vic Ciccolella, Oakville (AU)

(72) Inventor: Vic Ciccolella, Oakville (AU)

( * ) Notice: Subject to any disclaimer, the term of this patent is extended or adjusted under 35 U.S.C. 154(b) by 150 days.

(21) Appl. No.: 14/120,216

(22) Filed: May 6, 2014

(65) Prior Publication Data

US 2015/0327424 P1 Nov. 12, 2015

(51) Int. Cl.
*A01H 5/12* (2006.01)

(52) U.S. Cl.
USPC ..... Plt./424

(58) Field of Classification Search
USPC ..... Plt./424
See application file for complete search history.

*Primary Examiner* — Keith Robinson
(74) *Attorney, Agent, or Firm* — Samuel R. McCoy, Jr.

(57) ABSTRACT

'DCGL' is a distinctive variety of *Dianella caerulea* which is characterized by the presence of yellow and green leaf variegation and uniformity of traits through successive cycles of asexual propagation.

2 Drawing Sheets

Latin name of the genus and species: The Latin name of the genus and species of the novel variety disclosed herein is *Dianella caerulea.*

Variety denomination: The inventive variety of *Dianella caerulea* disclosed herein has been given the variety denomination 'DCGL'.

BACKGROUND OF THE INVENTION

The present invention relates to a new and distinct perennial variety of *Dianella caerulea*, which has been given the variety denomination of 'DCGL'. Its market class is that of an ornamental plant or grass-like plant. 'DCGL' is intended for use in landscaping and container gardening.

Parentage: In 2005, seed that resulted from an open pollination of a 'no-cane' form of *Dianella caerulea* (unnamed, unpatented) was sown at a nursery in Oakville, New South Wales, Australia and the resulting progeny were grown to a mature size. In February 2006, the selection now called 'DCGL' was observed to have green and yellow variegated foliage whereas the parent and other sibling progeny did not have variegated foliage; said selection was isolated for further observation. It was further grown, and subsequently observed from February 2006 until April 2013, at which time it was determined that the characteristics for which it was originally selected were uniform and stable.

Asexual Reproduction: In January 2007, 'DCGL' the selection was propagated by vegetative divisions and said divisions were grown to mature plants. These plants were subsequently divided in October 2007 to further increase numbers and test for stability. In 2011, 'DCGL' was initiated into tissue culture. It has been uniform and stable through all generations of division and subcultures. 'DCGL' was grown on between November 2011 and April 2013 and has shown that the characters for which it was selected are uniform and stable with no off types observed.

SUMMARY OF THE INVENTION

'DCGL' is a distinctive variety of *Dianella caerulea* which is characterized by the presence of yellow and green leaf variegation and uniformity of traits through successive cycles of asexual propagation.

BOTANICAL DESCRIPTION OF THE PLANT

Figure 1:
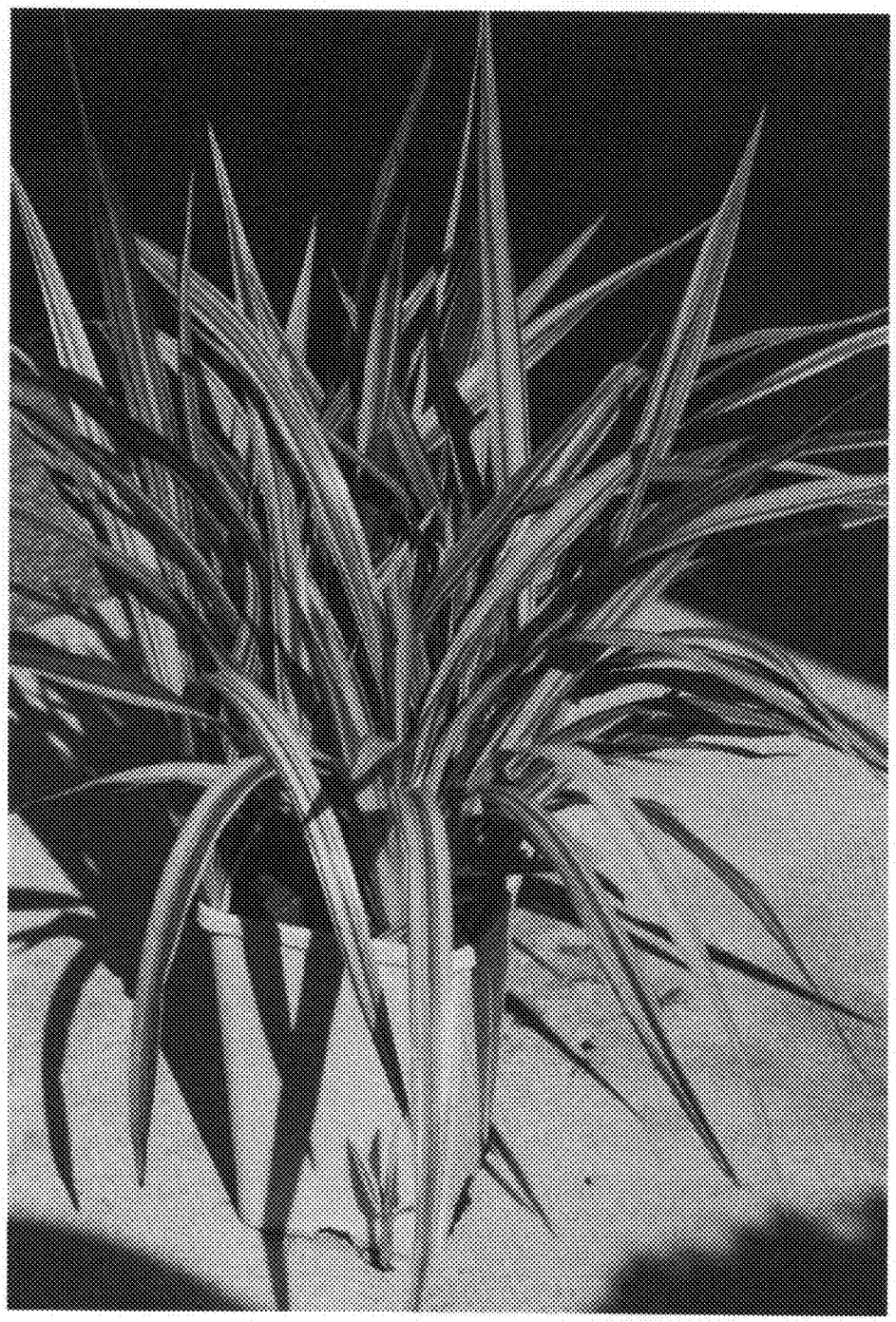
FIG. 1 illustrates an exemplary mature 'DCGL' plant at approximately 12 months old from a rooted cutting.
Figure 2:
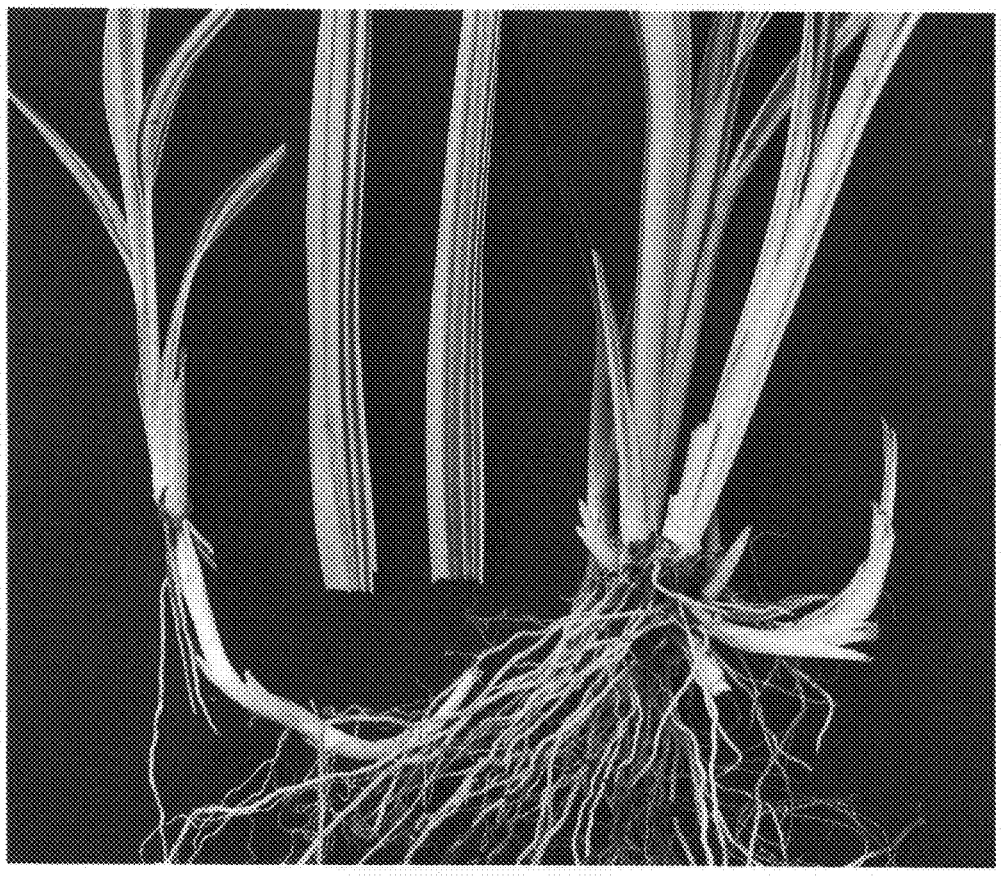
FIG. 2 illustrates the exemplary foliage variegation, the short rhizomes, and strong shoot density of 'DCGL'.

The following is a detailed botanical description of a new and distinct variety of a *Dianella caerulea* ornamental plant known as 'DCGL'. Plant observations were made on plants grown in New South Wales, Australia. Unless indicated otherwise, the descriptions disclosed herein are based upon observations made from mature, 12 month-old 'DCGL' plants grown from rooted cuttings from May 2012 to May 2013 in 200 mm nursery pots filled with soilless potting media, maintained with granular slow release fertilizer, and regularly watered with overhead irrigation. No pest and disease measures were taken.

Those skilled in the art will appreciate that certain characteristics will vary with older or, conversely, younger plants. 'DCGL' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Unless otherwise indicated, color notations are based on *The Royal Horticultural Society Colour Chart*, The Royal Horticultural Society, London, 2001 edition. Note that generic color descriptions such as 'yellow' do not exist in the R.H.S. charts and the corresponding R.H.S. colors are quoted.

Growth Habit, Dimensions and Color

Plant description:

*Plant habit.*—Semi-erect, grass-like perennial.

*Height.*—35 cm.

*Width*.—30 cm.
*Bloom period*.—Late spring in New South Wales, Australia.
*Hardiness*.—USDA Zone 9 to 11.
*Environmental tolerances*.—'DCGL' has not yet been observed under all conditions but has shown to be heat tolerant, adapting well to temperatures of 103 degrees Fahrenheit without any noticeable damage. It has survived light to moderate frosts and temperatures down to 23 degrees Fahrenheit.
*Drought tolerance*.—'DCGL' has not yet been observed under all conditions but it has shown good drought tolerance once established; typical of the species.
*Pest and disease susceptibility or resistance*.—No known pests.
*Propagation*.—Propagation is accomplished by dividing the rhizomatous crown of the plant.
*Time to produce a rooted cutting*.—3 weeks at approximately 68 degrees Fahrenheit.
*Crop time*.—From 4 to 7 months are needed to produce a well-rooted 200 mm pot, starting from a rooted cutting, depending on geographic location.

Stem:
*Branching habit*.—Acaulescent, rhizomatous plant with shoots emerging upright at 90 degrees from rhizomes.

Roots: Short, subsurface rhizomes which root at nodes; roots fibrous; root density is high.

Basal shoots:
*Shoots density*.—Numerous; more than 25 in a 200 mm nursery pot.
*Shoot strength*.—Strong.
*Cross section*.—Equitant.
*Shoot color*.—Cream, closest to 160D.
*Shoot dimensions*.—Newly emerging shoots with mean length of 21 mm and a mean diameter of 4.4 mm.
*Shoot surface*.—Smooth.

Foliage:
*Type*.—Evergreen.
*Arrangement*.—Equitant.
*Division*.—Simple.
*Shape*.—Linear.
*Apex*.—Acute.
*Base*.—Sheathed.
*Venation*.—Parallel.
*Vein color* (*adaxial surfaces*).—Vein color corresponds with surrounding foliage color; where foliage is green the vein color is closest to green RHS 146A, and where foliage is yellow the veins are also colored yellow, corresponding to RHS 12A.
*Vein color* (*abaxial surfaces*).—Vein color corresponds with surrounding foliage color; where foliage is green the vein color is closest to green RHS 146A, and where foliage is yellow the veins are also colored yellow, corresponding to RHS 12A.
*Margins*.—Serrulate.
*Attachment*.—Sessile.
*Texture*.—Smooth.
*Surfaces pubescence and luster* (*adaxial surface*).—Glabrous and slightly glossy.
*Surfaces pubescence and luster* (*abaxial surface*).—Glabrous and slightly glossy.
*Mature leaf dimensions*.—Average length 35 cm, average width 2.1 cm.
*Leaf color* (*adaxial & abaxial surfaces*).—Juvenile and mature foliage is variegated with approximately fifty percent of the leaf surface being green, corresponding closest to RHS 146A, and fifty percent being yellow, corresponding to RHS 12A.
*Petiole*.—Leaves are sessile.
*Stipules*.—Absent.

Inflorescence:
*Type*.—Lax panicles sit above the foliage in late spring.
*Natural flowering season*.—Late spring in New South Wales, Australia.
*Flowering habit*.—
*Inflorescence dimensions*.—Approximately 30 to 40 cm long and 25 to 32 cm wide.
*Inflorescence quantity*.—Potentially one inflorescence emerging from every shoot.
*Peduncle*.—Dimensions — Approximately 48 to 55 cm long and 0.5 mm wide at the base. Attitude — Upright. Color — Yellow-green RHS 144A. Texture and pubescence — Smooth; glabrous. Strength — Medium.
*Quantity of flowers per inflorescence*.—More than 30.

Bud:
*Dimensions*.—9 mm long and 4 mm wide.
*Shape*.—Ovoid; apex and base are obtuse.
*Color*.—A combination of greyed-purple RHS 186C, violet RHS 84C, and violet RHS 85C.

Flower:
*Flower type*.—Simple.
*Flower shape*.—Rotate; tepals are strongly reflexed.
*Diameter*.—Approximately 11 mm.
*Persistence*.—Not persistent.
*Flower aspect*.—Pendulous.
*Fragrance*.—Non-fragrant.
*Pedicels*.—Dimensions — 9 to 12 mm long and 2 mm wide. Color — Yellow-green RHS 144A, with slight intonations of greyed-purple RHS 186C. Texture and pubescence — Smooth; glabrous. Strength — Medium.
*Tepals*.—Quantity — Six. Arrangement — Whorled. Dimensions — 8 to 9 mm long and 3 to 3.5 mm wide. Fused or unfused — Unfused. Shape — Oblong. Margin — Entire; slightly undulate. Apex — Broad acute to obtuse. Base — Obtuse. Pubescence, texture, and luster — Glabrous, velvety; matte. Petal color when opening (upper side) — Violet RHS 85C. Petal color when opening (under side) — Violet RHS 85D. Petal color when fully opened (upper side) — Violet RHS 85C. Petal color when fully opened (under side) — Violet RHS 85D. Petal color fading to — Not fading.

Reproduction organs:
*Stamens*.—Quantity — Six. Anther — Attachment — Adnate. Shape — Narrowly oblong; apex is acute. Dimensions — 7 to 8 mm long and 2.5 mm wide. Color — Yellow RHS 9B. Filament — Dimensions — 2.5 mm long and 1.5 mm in diameter. Color — Yellow-white RHS 159D. Pollen — Light to medium density; black RHS 202A.
*Pistil*.—Quantity — One. Dimensions — 9 mm long and approximately 1 mm wide. Stigma — Shape — Papillose swelling at the apex of the style. Dimensions — Approximately 1.5 mm in diameter and 1 mm tall. Color — Violet RHS 84C. Style — Dimensions — Approximately 7 to 8 mm in diameter and 1 mm in diameter. Color — Violet RHS 84C. Ovary — Position — Superior. Dimensions — Approximately 3 to 3.5 mm in diameter and 2.5 mm tall. Color — Yellow-green RHS 144C.

Fruit and seed:
*Fruit*.—Shape — Globose. Dimensions — Approximately 8 to 9 mm long and 9 to 11 mm wide. Color — Violet-Blue RHS 89C to 89D. Texture and luster — Smooth and glossy.

*Seed*.—Quantity — Six. Shape — Ovoid. Dimensions — 5 to 3 mm long and 1.5 mm wide. Color — Black RHS 202A.

Comparison of DCGL with Other Varieties of *Dianella caerulea*

While there are several variegated forms of the Genus known to the breeder, 'DCGL' is the only variegated form of this species, making the parent plant the closest available comparator.

'DCGL' is very similar to the parent plant, a 'no-cane' form of *Dianella caerulea* (unnamed, unpatented), in most respects except for leaf color. 'DGCL' has a yellow and green leaf variegation corresponding to RHS 12A and RHS 146A, respectively, whereas the parent plant has solid green foliage, corresponding to 146A.

That which is claimed is:

1. A new and distinct variety of *Dianella caerulea* plant named 'DCGL', substantially as described and illustrated herein.

* * * * *